United States Patent [19]

Cherry et al.

[11] Patent Number: 5,578,630

[45] Date of Patent: Nov. 26, 1996

[54] HETEROCYCLIC COMPOUNDS WHICH INHIBIT AROMATASE

[75] Inventors: Peter C. Cherry; Michael W. Foxton; Andrew T. Merritt, all of Greenford, Great Britain

[73] Assignee: Glaxo Group Limited, London, Great Britain

[21] Appl. No.: 338,510

[22] PCT Filed: Jun. 14, 1993

[86] PCT No.: PCT/EP93/01520

§ 371 Date: Nov. 25, 1994

§ 102(e) Date: Nov. 25, 1994

[87] PCT Pub. No.: WO93/25548

PCT Pub. Date: Dec. 23, 1993

[30] Foreign Application Priority Data

Jun. 17, 1992 [GB] United Kingdom ............. 9212833

[51] Int. Cl.[6] .................. A61K 31/41; C07D 405/06
[52] U.S. Cl. ........................ 514/383; 548/266.4
[58] Field of Search ................ 514/383; 548/266.4

[56] References Cited

FOREIGN PATENT DOCUMENTS 0257171 3/1988 European Pat. Off. .
0316097 5/1989 European Pat. Off. .

*Primary Examiner*—Patricia L. Morris
*Attorney, Agent, or Firm*—Bacon & Thomas

[57] ABSTRACT

This invention relates to heterocyclic compounds which are inhibitors of the enzyme aromatase, to processes for their preparation, to pharmaceutical compositions containing them and to their use in medicine.

Particular compounds of the invention are compounds of formula (I)

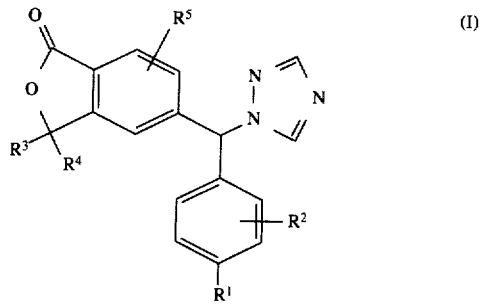

wherein $R^1$ represents a cyano or nitro group;

$R^2$ represents hydrogen or one or more halogen atoms;

$R^3$ represents a $C_{1-6}$alkyl group and $R^4$ represents hydrogen or a $C_{1-6}$alkyl group or $R^3$ and $R^4$ together represent a $C_{3-6}$cycloalkyl group; and $R^5$ represents hydrogen or one or more halogen atoms or $C_{1-6}$alkoxy groups and pharmaceutically acceptable salts and solvates thereof.

18 Claims, No Drawings

HETEROCYCLIC COMPOUNDS WHICH INHIBIT AROMATASE

This application is a 371 of PCT/EP 93/01520 filed Jun. 14, 1993.

This invention relates to heterocyclic compounds which are inhibitors of the enzyme aromatase, to processes for their preparation, to pharmaceutical compositions containing them and to their use in medicine.

Oestrogens are responsible for many physiological functions in both females and males. Their action is mediated by specific intracellular hormone receptors expressed in oestrogen responsive cells. Oestradiol, the major oestrogen, is produced from oestrone which in turn is produced from androstenedione by aromatization of the A-ring. This reaction is catalysed by the predominantly ovarian enzyme aromatase although in post menopausal women aromatase located in adipose tissue is responsible for the synthesis of oestrogens (O'Neill and Miller, Br.J.Cancer (1987)).

Oestrogens are agonists in responsive tissues, such as breast, and are a major factor in the development of breast tumours. Thus, aromatase inhibitors have valuable therapeutic potential for the treatment of oestrogen responsive diseases, particularly breast cancer (Brodie, ISI Atlas of Science: Pharmacology (1987) 266–269 and Santen et al., J. Lab. Clin. Med. (1987) 109: 278–289) and have been the subject of active research world-wide, see for example, the work of Schieweck et al., Cancer Res. (1988) 48: 834–838; Wouters et al, J. Steroid Biochem., (1989) 32: 781–788; Bhatnagar et al., J. Steroid Biochem., (1990) 37: 1021–1027.

We have now found a novel group of compounds which are potent and selective aromatase inhibitors.

Thus the present invention provides a compound of general formula (I)

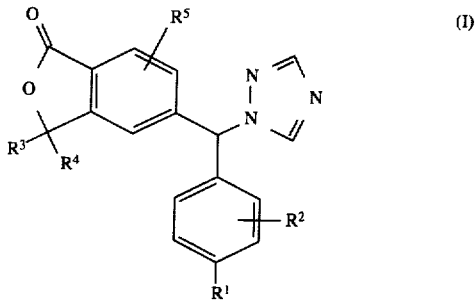

wherein $R^1$ represents a cyano or nitro group;

$R^2$ represents hydrogen or one or more halogen atoms;

$R^3$ represents a $C_{1-6}$alkyl group and $R^4$ represents hydrogen or a $C_{1-6}$alkyl group or $R^3$ and $R^4$ together represent a $C_{3-6}$cycloalkyl group; and $R^5$ represents hydrogen or one or more halogen atoms or $C_{1-6}$alkoxy groups and pharmaceutically acceptable salts and solvates thereof.

As used herein an alkyl or alkoxy group may be a straight or branched chain group, for example an alkyl group is conveniently a methyl, ethyl, propyl, isopropyl or butyl group. Halogen atom include fluorine, chlorine and bromine atoms.

The compounds of formula (I) contain at least one chiral carbon atom. It is to be understood that formula (I) is intended to encompass all enantiomers of the compounds of the invention as well as mixtures thereof, including racemic mixtures.

In a preferred group of compounds of formula (I) $R^2$ represents hydrogen or one or more halogen atoms selected from chlorine or fluorine, preferably one or two fluorine atoms in the meta position of the benzene ring relative to substituent $R^1$.

In a further preferred group of compounds of formula (I) $R^3$ and $R^4$ each independently represents a $C_{1-6}$alkyl group, especially a $C_{1-3}$alkyl group such as a methyl group.

In a further preferred group of compounds of formula (I) $R^5$ represents hydrogen or one or more halogen atoms selected from chlorine or fluorine, preferably fluorine, or $C_{1-3}$alkoxy groups, preferably methoxy.

Compounds of formula (I) wherein $R^5$ is other than hydrogen are preferably substituted in the 2 and/or 4-positions of the aromatic ring. However, compounds of formula (I) wherein $R^5$ is hydrogen are particularly preferred.

In a particularly preferred group of compounds of formula (I) $R^1$ represents a cyano or nitro group, $R^2$ represents hydrogen or one or two fluorine atoms in the meta position of the benzene ring relative to substituent $R^1$, $R^3$ and $R^4$ each represent a methyl group and $R^5$ represents hydrogen.

Preferred compounds according to the invention include

5-[(2,6-difluoro-4-nitrophenyl)-1,2,4-triazol-1-ylmethyl]-3,3-dimethyl-3H-isobenzofuran-1-one;

5-[(2-fluoro-4-nitrophenyl)-1,2,4-triazol-1-ylmethyl]-3,3-dimethyl-3H-isobenzofuran-1-one;

4-[(3,3-dimethyl-1-oxo-1,3-dihydro-isobenzofuran-5-yl)-1,2,4-triazol-1-ylmethyl]-3,5-difluorobenzonitrile;

5-[(4-nitrophenyl)-1,2,4-triazol-1-ylmethyl]-3,3-dimethyl-3H-isobenzofuran-1-one;

4-[(3,3-dimethyl-1-oxo-1,3-dihydro-isobenzofuran-5-yl)-1,2,4-triazol-1-ylmethyl]-3-fluorobenzonitrile; and 4-[(3,3-dimethyl-1-oxo-1,3-dihydro-isobenzofuran-5-yl)-1,2,4-triazol-1-ylmethyl]-benzonitrile, including individual enantiomers and racemic mixtures thereof and their pharmaceutically salts and solvates.

A particularly preferred compound according to the invention is 5-[(2,6-difluoro-4-nitrophenyl)-1,2,4-triazol-1-ylmethyl]-3,3-dimethyl-3H-isobenzofuran-1-one and its pharmaceutically acceptable salts and solvates.

Suitable pharmaceutically acceptable salts of the compounds of formula (I) include acid addition salts derived from inorganic and organic acids, such as hydrochlorides, hydrobromides, sulphates, phosphates, citrates, tartrates, maleates, fumarates, succinates, p-toluenesulphonates and mathanesulphonates. Other suitable salts will be readily apparent to one skilled in the art. Hydrochloride, sulphate and phosphate salts are especially preferred. Salts which are not pharmaceutically acceptable may be useful in the preparation of compounds of formula (I) and these form a further part of the invention.

Compounds of the invention may be isolated in association with solvent molecules by crystallisation from or evaporation of an appropriate solvent such solvates of the compounds of formula (I) are included within the scope of the present invention.

References hereinafter to a compound according to the invention includes both the compounds of formula (I) and their pharmaceutically acceptable salts and solvates.

The compounds according to the invention are potent and selective inhibitors of the enzyme aromatase, a key enzyme involved in the conversion of androgens into the female sex hormones oestrone and oestradiol.

Inhibitors of aromatase reduce circulating and local levels of oestrone and oestradiol. The compounds of the invention can thus be used in the treatment of oestrogen-dependant diseases such as malignant and benign diseases of the breast, endometrium, ovary, prostate and pancreas. These diseases include cancer of the breast and endometrium, fibrocystic breast disease, endometriosis, polycystic ovarian disease and prostatic hypertrophy and hyperplasia. The compounds of formula (I) are also useful in the treatment of Cushing's syndrome, gynecomastia, premature labour, precocious puberty, feminising adrenal tumours, male infertility associated with oligospermia and male impotence. Also, the compounds of the invention are of use in female fertility control, by inhibiting ovulation and egg nidation. The compounds according to the invention will be particularly useful in the treatment of oestrogen-responsive breast tumours in women.

The invention thus further provides compounds of formula (I) and their pharmaceutically acceptable salts and solvates for use as active therapeutic agents, in particular for the treatment of conditions where a lowering of the levels of oestrone and/or oestradiol in animals (especially humans) would be beneficial.

In a particular aspect of the present invention there is provided a compound of general formula (I) or a pharmaceutically acceptable salt or solvate thereof for use in the treatment of oestrogen-responsive breast tumours in women.

In a further or alternative aspect there is provided a method for the treatment of a mammal, including human, comprising administration of an effective amount of a compound of formula (I) or a pharmaceutically acceptable salt or solvate thereof, in particular to lower oestrone and/or oestradiol levels.

There is also provided in a further or alternative aspect use of a compound of formula (I) or a pharmaceutically acceptable salt or solvate thereof for the manufacture of a medicament for the lowering of oestrone and/or oestradiol levels in a mammal including a human.

It will be appreciated by those skilled in the art that reference herein to treatment extends to prophylaxis as well as the treatment of established symptoms.

While it is possible that, for use in therapy, a compound of the invention may be administered to a patient as the raw chemical, it is preferable to present the active ingredient as a pharmaceutical formulation.

The invention accordingly provides a pharmaceutical formulation comprising a compound of formula (I) or a pharmaceutically acceptable salt or solvate thereof together with one or more pharmaceutically acceptable carriers or excipients and, optionally, other therapeutic and/or prophylactic ingredients. The carriers must be "acceptable" in the sense of being compatible with the other ingredients of the formulation and not deleterious to the recipient thereof.

Pharmaceutical formulations include those suitable for oral, rectal, nasal, topical, implant or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-, p-hydroxybenzoates or sorbic acid).

For topical administration in the mouth, the pharmaceutical compositions may take the form of buccal or sublingual tablets, drops or lozenges formulated in conventional manner.

For topical administration to the epidermis the compounds of the invention may be formulated as creams, gels, ointments or lotions or as transdermal patches. Such compositions may, for example, be formulated with an aqueous or oily base with the addition of suitable thickening, gelling, emulsifying, stabilising, dispersing, suspending, and/or colouring agents.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

For intranasal administration the compounds of the invention may be used, for example, as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, 1,1,1,2-tetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Any of the pharmaceutical compositions described above may be presented in a conventional manner associated with controlled release forms.

Preferably the pharmaceutical compositions according to the invention are suitable for oral, rectal or topical administration.

A convenient unit dose formulation contains the active ingredient in an amount of from 0.1 to 200 mg.

It will be appreciated that the amount of a compound of formula (I) required for use in treatment will vary not only with the particular compound selected, but also with the route of administration, the nature of the condition being treated and the age, weight and condition of the patient and will ultimately be at the discretion of the attendant physician or veterinarian. In general, however, a suitable dose will be in the range of from about 0.1 to about 200 mg per day, preferably in the range of 0.5 to 50 mg per day, most preferably in the range of 1 to 20 mg per day.

A suitable daily dose for use in prophylaxis will generally be in the range of 0.1 mg to 25 mg.

The desired dose may conveniently be presented in a single dose or as divided doses administered at appropriate intervals, for example as two, three, four or more sub-doses per day. The compound is conveniently administered in unit dosage form.

The compounds of the present invention may also be used in combination with other therapeutic agents, for example, other anticancer agents. In particular the compounds of the invention may be employed together with known anticancer agents.

The invention thus provides, in a further aspect, a combination comprising a compound of formula (I) as defined herein together with another therapeutically active agent, in particular an anticancer agent.

The combination referred to above may conveniently be presented for use in the form of a pharmaceutical formulation and thus pharmaceutical formulations comprising a combination as defined above together with a pharmaceutically acceptable carrier therefor comprise a further aspect of the invention.

When compounds of formula (I) are used in combination with a second therapeutic agent, the active compounds may be administered either sequentially or simultaneously by any of the routes described above.

Suitable therapeutic agents for use in the combinations defined above include, for example alkylating agents such as cyclophosphamide, antimetabolites such as methotrexate, mitotic inhibitors such as vinblastine, antitumour antibiotics such as adriamycin, endocrine therapy such as tamoxifen, flutamide, goserelin acetate and medroxyprogesterone acetate, radiotherapy and immunotherapy.

When compounds of formula (I) are used in combination with a second therapeutic agent the dose of each active compound may vary from that when the compound is used alone. Thus when compounds of formula (i) are used together with a second therapeutic agent the dose of each active compound may be the same or different to that employed when the compound is used alone. Appropriate doses will be readily appreciated by those skilled in the art.

The compounds according to the invention may be prepared by any process known in the art for the preparation of compounds of analogous structure. In the following description $R^1$, $R^2$, $R^3$, $R^4$ and $R^5$ are as defined for general formula (I) unless otherwise specified.

In one general process A a compound of formula (I) may be prepared from an intermediate of formula (II)

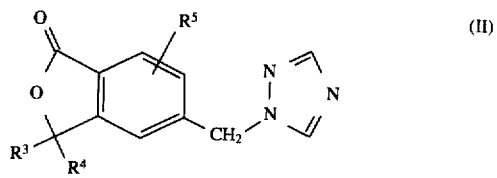

by reaction in the presence of a strong base (e.g. potassium tert-butoxide) with a compound of formula (III)

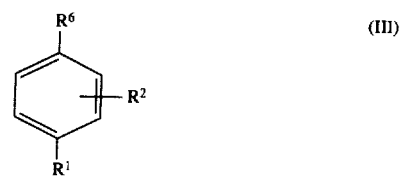

wherein $R^6$ is a group susceptible to displacement by the benzyl lactone anion

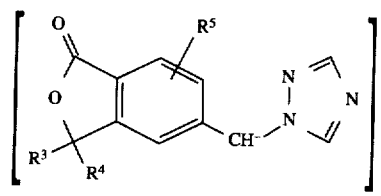

formed in situ. Suitable $R^6$ groups susceptible to displacement by the benzyl lactone anion include hydrogen or halogen atom, sulphonate ester groups such as methanesulphonate, para-toluenesulphonate and trifluoromethanesulphonate, and diazonium groups. Advantageously $R^6$ is a hydrogen or halogen atom e.g. a fluorine atom. The reaction is conveniently carried out in a suitable reaction medium such as an anhydrous solvent e.g. N,N-dimethylformamide.

The intermediates of formula (II), in particular 3,3-dimethyl-5-[1,2,4-triazol-1-ylmethyl]-3H-isobenzofuran-1-one, are novel compounds and represent a further aspect of the present invention.

The intermediate of formula (II) may be prepared from an intermediate of formula (IV)

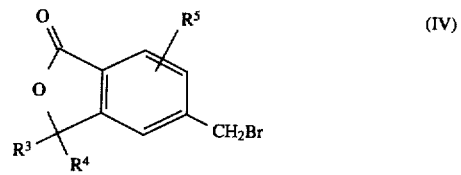

by reaction with a compound of formula (V)

or a salt, such as an alkali metal salt e.g. a sodium salt thereof. The reaction is conveniently carried out in a suitable reaction medium such as an anhydrous solvent e.g. anhydrous N,N-dimethylformamide or acetone.

The compound of formula (IV) may be prepared from a compound of formula (VI)

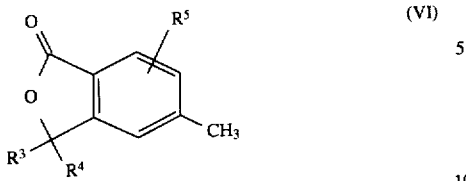

by free radical bromination, for example using N-bromosuccinamide in the presence of an initiator such as 2,2'-azobis(2-methylproprionitrile) and/or ultraviolet light. The reaction is conveniently carried out in a suitable reaction medium such as tetrachloromethane.

The compound of formula (VI) may be prepared from a compound of formula (VII)

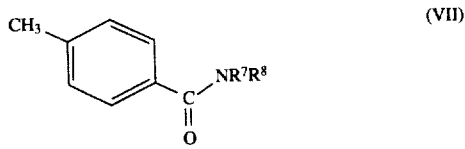

wherein $R^7$ and $R^8$ each independently represent hydrogen or a $C_{1-6}$ alkyl group, by reaction with a strong base such as N-butyllithium in a suitable reaction medium such as tetrahydrofuran, followed by treatment with a compound of formula (VIII)

Thus, for example, a compound of formula (VI) wherein $R^3$ and $R^4$ both represent a methyl group may be prepared by reaction of a compound of formula (VII) with acetone.

Preferably $R^7$ represents hydrogen and $R^8$ represents methyl, ethyl or propyl.

According to another general process B a compound of formula (I) may be converted into another compound of formula (I) using conventional procedures.

According to another general process C a compound of formula (I) may be prepared by subjecting a protected derivative thereof to reaction to remove the protecting group or groups. Thus, at an earlier stage in the reaction sequence it may have been necessary or desirable to protect one or more sensitive groups in the molecule to avoid undesirable side reactions. Such protection may be effected in conventional manner, for example as described in "Protective Groups in Organic Chemistry" Ed. JFW McOmie (Plenum Press 1973) or "Protective Groups in Organic Synthesis" by T W Green (John Wiley & Sons 1981).

Where it is desired to isolate a compound of the invention as a salt, for example as an add addition salt, this may be achieved by treating the free base of formula (I) with an appropriate add in conventional manner. Solvates of the compounds of the invention may be prepared by crystallisation from or evaporation of an appropriate solvent solution of the compounds of formula (I). Separation of enantiomers of formula (I) may be carried out in conventional manner, for example by resolution of racemic mixtures e.g. using chiral HPLC techniques or by stereospecific synthesis from isomerically pure starting material or any convenient intermediate, for example as described in Stereochemistry of Carbon Compounds by E. L. Eliel (McGraw Hill, 1962) and Tables of Resolving Agents by S. H. Wilen.

Thus according to a further aspect of the invention the following steps may, if necessary and/or desired, be carried out in any appropriate sequence subsequent to any of the processes A to B:

(i) removal of any protecting groups;

(ii) conversion of a compound of formula (I) or a salt or solvate thereof into a pharmaceutically acceptable salt or solvate thereof;

(iii) separation of a racemic mixture into individual enantiomers of formula (I).

As indicated above the compounds of the invention are useful as aromatase inhibitors. Aromatase inhibition may be demonstrated by the following tests:

ACTIVITY in vitro

Aromatase inhibitory activity may be determined using human placental aromatase.

Human placental aromatase was assayed according to the method of Thomson and Siiteri, Hormone Res. (1979) 11: 179–185, except that the assay buffer contained 1 mM NADPH instead of the NADPH-generating system. [$^3$H]-$H_2O$, released as a by-product of aromatization, was separated from substrate using C18 mini-columns.

The results of this assay (expressed as $IC_{50}$ values) for the compounds of the following examples are shown in Table 1.

TABLE 1

| Aromatase inhibitory activity - in vitro | |
|---|---|
| Example | $IC_{50}$ (μM) |
| 1 | 0.015 |
| 2 | 0.063 |
| 3 | 0.024 |
| 5 | 0.051 |
| 6 | 0.083 |
| 7 | 0.073 |

In vitro selectivity was assessed by comparing the inhibitory effects of test compounds against aromatase and human adrenal 11β-hydroxylase. The latter was determined according to the method of Kawamoto et al. (1990), Biochem. Biophys. Res. Commun. 173, 309–316 using a mitochondrial preparation of human adrenal cortex as an enzyme source, [1,2-$^3$H(N)]11-deoxycortisol as substrate and 1 mM NADPH as cofactor. [1,2-$^3$H(N)]-Cortisol was separated from the substrate using PH mini-columns which were solvated prior to the application of assay mixture. [1,2-$^3$H(N)]-Cortisol was eluted with 35% v/v methanol in water.

In the above in vitro tests the preferred compounds of formula (I) are potent and selective aromatase inhibitors.

ACTIVITY—in vivo

In vivo activity and selectivity were determined by comparing the effects of compounds of the invention on oestrogen and aldosterone levels in rats. Oestrogen levels were measured in PMSG-primed rats according to the method of Brodie (1982), Cancer Res. (Suppl.) 42:33605–33645, except that priming was performed over a 9 day period and circulating, rather than ovarian, oestrogen levels were determined.

Compounds of the invention were evaluated for their inhibitory activity on aldosterone production in rats treated with ACTH sc. (see, for example, review by Fraser et al., Clinical Science (1979) 56, 389–399). Test compounds were administered p.o. 2 h prior to 0.5 IU ACTH and the animals sacrificed after 30 min. Effects on serum aldosterone levels, determined by radioimmunoassay, taken together with effects on serum oestrogen levels provided information on the selectivity of aromatase inhibition by test compounds.

In the above in vivo tests the preferred compounds of formula (I) are potent and selective aromatase inhibitors.

Acute toxicity studies indicate that single doses of the compound of Example 1 up to 2 g/kg p.o. are well tolerated in the mouse.

The following non-limiting examples illustrate the invention. Temperatures are in ° C. Dried means dried over anhydrous magnesium sulphate unless otherwise stated.

Intermediate 1

3.3-Dimethyl-5-[1,2,4-triazol-1-ylmethyl]-3H-isobenzofuran-1-one

Preparation A a) To N-methyl-4-toluamide (36.5 g) in tetrahydrofuran (500 ml) at 0° under nitrogen was added n-butyl lithium (205 ml of 2.5M solution in hexanes) over 20 minutes and the resulting solution was stirred for 80 minutes at 0°. Acetone (77 ml) was added, keeping the reaction temperature below 5° and the mixture was stirred for one hour before glacial acetic add (14 ml) was added. After warming to room temperature for one and a half hours the reaction was poured into 1M hydrochloric add (500 ml) and extracted with ethyl acetate. The combined organic extracts were washed with brine, dried then evaporated until unreacted staffing amide began to crystallise out at the boiling point. The mixture was allowed to cool, the amide was filtered off and the mother-liquors were evaporated to a brown oil which was purified by column chromatography on Merck 7734 silica, eluting with cyclohexane:ethyl acetate (6:1) to give the desired lactone 3,3,5-trimethyl-3H-isobenzofuran-1-one, as a white solid.

IR (CHBr$_3$) 1751 cm$^{-1}$.

NMR (CDCl$_3$) δ7.74 (d, 1H, H7), 7.31 (d, 1H, H6), 7.20 (s, 1H, H4), 2.50 (s, 3H, CH$_3$), 1.65 (s, 6H, C(CH$_3$)$_2$).

MS [MH]$^+$=177 [MNH$_4$]$^+$=194.

b) 3,3,5-Trimethyl-3H-isobenzofuran-1-one (13.6 g) was dissolved in carbon tetrachloride (500 ml) and to this solution was added N-bromosuccinimide (15.1 g) and α-azo-iso-butyronitrile (0.13 g). The reaction mixture was irradiated with a 150 W tungsten lamp for one hour then cooled, filtered and the filtrate evaporated to an oil. The oil was dissolved in N,N-dimethylformamide (150 ml), the sodium salt of 1,2,4-triazole (13.8 g) added and the mixture stirred overnight. The mixture was partitioned between water and ethyl acetate and the phases separated. The aqueous phase was extracted with ethyl acetate and the combined organic extracts were washed with water, brine, dried and then evaporated to a brown oil. The crude material was purified by column chromatography on Merck 9385 silica eluting with dichloromethane:methanol (20:1) to give the desired product, 3,3-dimethyl-5-[1,2,4-triazol-1-ylmethyl]-3H-isobenzofuran-1-one as a red-brown oil.

IR (CHBr$_3$) 1756, 1667, 1503 cm$^{-1}$.

NMR (CDCl$_3$) δ8.21 (s, 1H, triazole), 8.02 (s, 1H, triazole), 7.87 (d, 1H, H7), 7.38 (d, 1H, H6), 7.24 (s, 1H, H4), 5.50 (s, 2H, CH$_2$), 1.64 (s, 6H C(CH$_3$)$_2$).

MS (NC FILM) [MH]$^+$=244.2, 228.0, 175.3.

Preparation B a) A suspension of N-methyl-4-toluamide (100 g) in anhydrous tetrahydrofuran (2 l) was cooled to −28° and n-butyl lithium (580 ml of 2.5M solution in hexanes) was added dropwise maintaining the temperature at −20° to −25°. The resultant solution was stirred at −20° for 2 h, then cooled to −42° and acetone (175 ml) added dropwise maintaining the temperature below −42°. Stirring was continued at −35° to −42° for 1 h before glacial acetic add (39 ml) was added. The mixture was stirred without further cooling for 90 min and then poured into aqueous HCl (1N, 1.4 l) and ethyl acetate (0.5 l). The organic phase was washed with brine (3'1 l), dried over sodium sulphate and concentrated and dried in vacuo. The solid was dissolved in hot methylene chloride (350 ml) and cooled to 3°. The filtrate was treated with hexane (50 ml) and cooled to 3°. The filtrate was dissolved in methylene chloride (1 l) and heated to reflux in the presence of aqueous HCl(6N, 1 l) for 6 h. The organic phase was separated and again heated to reflux in the presence of aqueous HCl (6N, 1 l) for 7 h. The organic phase was separated and washed with saturated aqueous sodium bicarbonate (2'1 l) and concentrated in vacuo to give 3,3,5 -trimethyl-3H-isobenzofuran-1-one. HPLC and NMR data were consistent with the product obtained in Preparation A (a) and with its structure.

b) 3,3,5-Trimethyl-3H-isobenzofuran-1-one (200 g) was dissolved in anhydrous carbon tetrachloride (8 l), N-bromosuccinimide (220 g) and α-azo-iso-butyronitrile (4.0 g). The mixture was heated to reflux under nitrogen for 5.5 h, cooled to room temperature and filtered. The clear yellow filtrate was washed with aqueous HCl (1N, 4 l), then water (4 l) and the organic phase dried over sodium sulphate, concentrated to a yellow solid and further dried under high vacuum.

The sodium salt of 1,2,4-triazole (10.4 g) and anhydrous acetone (250 ml) was added to the reaction mixture and stirred at room temperature for 4 hours. Sodium bromide was removed by filtration and the filtrate concentrated to a brown oil. The oil was dissolved in ethyl acetate (150 ml) and stirred in the presence of aqueous HCl (3N, 40 ml) for 20 min. The aqueous phase was separated and treated with ethyl acetate (150 ml). Aqueous NaOH (6N, 20 ml) was added dropwise with stirring maintaining the temperature below 35°. The organic layer was separated and concentrated in vacuo to give 3,3-dimethyl-5-[1,2,4-triazol-1-ylmethyl]-3H-isobenzofuran-1-one. HPLC and NMR data ware consistent with the product obtained in Preparation A (b) and with its structure.

Example 1

5-[(2,6-Difluoro-4-nitrophenyl)-1,2,4-triazol-1-ylmethyl]-3.3-dimethyl-3H-isobenzofuran-1-one To a solution of 3,3-dimethyl-5-[1,2,4-triazol-1-ylmethyl]-3H-isobenzofuran-1-one (4.47 g Intermediate 1) in N,N-dimethylformamide (250 ml) at 0° under nitrogen was added potassium tert-butoxide (4.53 g). After one hour 3,5-difluoronitrobenzene (3.22 g) was added and stirring continued for five hours. The reaction mixture was partitioned between water and ethyl acetate and the phases separated. The aqueous phase was extracted with ethyl acetate and the combined organic extracts were washed with water and brine, dried and then evaporated to yield a brown oil. This was purified by column chromatography on Merck 9385 silica eluting initially with dichloromethane through to a 50:1 mixture of dichloromethane:methanol to yield a brown foam. The brown foam was further purified by gradient elution HPLC (water-acetonitrile-trifluoroacetic acid) to give 5-[(2,6-difluoro-4-nitrophenyl)-1,2,4-triazol-1-ylmethyl]-3,3-dimethyl-3H-isobenzofuran-1-one as a yellow foam.

IR (CHBr$_3$) 1760, 1539 cm$^{-1}$.

NMR (CDCl$_3$) δ8.15 (s, 1H, triazole), 8.00 (s, 1H, triazole), 7.93 (d, 3H, H3', H5', H7), 7.36 (d, 1H, H6), 7.24 (s, 1H, H4), 7.18 (s, 1H, CH), 1.54 (s, 6H, C(CH$_3$)$_2$).

MS (+ve FAB) 401 [MH]$^+$100%, 332 48%.

Example 2

5-[(2-Fluoro-4-nitrophenyl)-1,2,4-triazol-1-ylmethyl]-3,3-dimethyl-3H-isobenzofuran-1-one By a procedure similar to that described in Example 1 5-[(2-fluoro-4-nitrophenyl)-1,2,4-triazol-1-ylmethyl]-3,3-dimethyl-3H-isobenzofuran-1-one was prepared.

IR (Nujol) 1741, 1566 cm$^{-1}$.

NMR (CDCl$_3$) δ8.20 (1H,s,triazole), 8.11 (1H,s,triazole), 8.07 (2H,m,H3',H5'), 7.90 (1H,d,H7), 7.39 (2H,m,H6, H6'), 7.25 (1H,s,H4) 7.16 (1H,s,CH), 1.67 (3H,s,C—CH$_3$), 1.66 (3H,s,C—CH$_3$).

M.S. (+FAB) 383(MH)$^+$80%,314 100%.

Example 3

4-[(3,3-Dimethyl-1-oxo-1,3-dihydro-isobenzofuran-5-yl)-1,2,4-triazol-1-ylmethyl]-3,5-difluorobenzonitrile, By a procedure similar to that described in Example 1 4-[(3,3-dimethyl-1-oxo-1,3-dihydro-isobenzofuran-5-yl)-1,2,4-triazol-1-ylmethyl]-3,5-difluorobenzonitrile was prepared.

NMR (CDCl$_3$) δ8.12(1H,s,triazole) 8.08(1H,s,triazole), 7.90(1H,d,H7), 7.34(3H,m,H3',H5',H6), 7.21 (1H,s,H4), 7.17 (1H,s,CH), 1.64(6H,s,C(CH$_3$)$_2$).

M.S. (PD.TOF) 381.4[MH]$^+$, 312.3, 149.2.

Example 4 a) (R)-5-[(2,6-Difluoro-4-nitrophenyl)-1,2,4-triazole-1-ylmethyl]-3,3-dimethyl-3H-isobenzofuran-1-one b) (S)-5-[(2,6-Difluoro-4-nitrophenyl)-1,2,4-triazole-1-ylmethyl]-3,3-dimethyl-3H-isobenzofuran-1-one The racemic mixture of Example 1 was separated by HPLC by eluting with heptane:isopropanol:trifluoroacetic acid (80:20:0.5) on a Chiracel AD column. Concentration of the relevant fractions gave the separate enantiomers as the trifluoroacetic acid salts with an ee of >80%.

Each trifluoroacetic acid salt was partitioned between saturated aqueous sodium bicarbonate and ethyl acetate. The organic phase was separated, washed with brine, dried and evaporated to give the enantiomeric compounds in the form of the free base. Whilst the two enantiomers were not completely separated the compound of Example 4(a) was isolated as a yellow solid, [α]$_D$=−38.25° and the compound of Example 4(b) as a yellow oil [α]$_D$=+15.43°.

Example 5

5-[(4-Nitrophenyl)-1,2,4-triazol-1-ylmethyl]-3,3-dimethyl-3H-isobenzofuran-1-one 3,3-Dimethyl-5-[1,2,4-triazol-1-ylmethyl]-3H-isobenzofuran-1-one (200 mg, Intermediate 1) was dissolved in N,N-dimethylformamide (8 ml) at 0° under nitrogen and potassium tert-butoxide was added (138 mg). After 30 minutes 4-fluoronitrobenzene (232 mg) in N,N-dimethylformamide (1 ml) was added and stirring continued for one hour. The mixture was warmed to room temperature, stirred for one hour then partitioned between water and ethyl acetate. The aqueous phase was extracted with ethyl acetate then the combined organic extracts were washed with water, brine, dried then evaporated to a yellow solid. The crude material was purified by column chromatography on Merck 9385 silica eluting with dichloromethane:methanol (50:1) to give a yellow oil, 5-[(4-nitrophenyl)-1,2,4-triazol-1-ylmethyl]-3,3-dimethyl-3H-isobenzofuran-1-one.

NMR (CDCl$_3$) δ8.27 (2H, d, H3'), 8.20 (1H, s, triazole), 8.10 (1H, s, triazole), 7.90 (1H, d, H7), 7.40 (3H, m, H6, H2'), 7.27 (1H, s, H4), 7.00 (1H, s, CH), 1.65 (6H, s, C(CH$_3$)$_2$).

MS (EI) 364 M$^+$(22%), 349 (100%), 296 (10%), 280 (18%).

Example 6

4-[(3,3-Dimethyl-1-oxo-1,3-dihydro-isobenzofuran-5-yl)-1,2,4-triazol-1-ylmethyl]-3-fluorobenzonitrile By a procedure similar to that described in Example 5 4-[(3,3-dimethyl-1-oxo-1,3-dihydro-isobenzofuran-5-yl)-1,2,4-triazol-1-ylmethyl]-3-fluorobenzonitrile was prepared.

IR(CHBr$_3$) 2339, 1670cm$^{-1}$.

NMR(CDCl$_3$) δ8.20(1H,s,triazole), 8.08(1H,s,triazole), 7.90(1H,d,H7), 7.50(2H,m,H2',H6'), 7.33(2H,m,H6, H5'), 7.21(1H,s,H4), 7.15(1H,s,CH), 1.69(3H,s,C—CH$_3$), 1.68(3H,s,C—CH$_3$).

M.S.(PD.TOF) 363.4[MH]$^+$, 294.2, 1.89.2.

Example 7

4-[(3,3-Dimethyl-1-oxo-1,3-dihydro-isobenzofuran5-yl)-1,2,4-triazol-1-ylmethyl]-benzonitrile By a procedure similar to that described in Example 5 4-[(3,3-dimethyl-1-oxo-1,3-dihydro-isobenzofuran-5-yl)-1,2,4-triazol-1-ylmethyl]-benzonitrile was prepared.

IR(CHBr$_3$) 2255, 1758cm$^{-1}$.

NMR(CDCl$_3$) δ8.21 (1H,s,triazole), 8.20(1H,s,triazole), 7.89(1H,d,H7) 7.70(2H,d,H2',H6'), 7.30(3H,m,H3', H5',H6), 7.19(1H,s,H4), 6.87(1H,s,CH), 1.63(6H,s, C(OH$_3$)$_2$).

M.S. (PD.TOF) 345.3[MH]$^+$, 382[MK]$^+$, 276.3.

Example 8 a) (R)-4-[(3,3-dimethyl-1-oxo-1,3-dihydro-isobenzofuran-5-yl)-1,2,4-triazol-1-yl methyl]-benzonitrile b) (S)-4-[(3,3-dimethyl-1-oxo-1,3-dihydro-isobenzofuran-5-yl), 1,2,4-triazol-1-yl methyl]-benzonitrile The racemic mixture of Example 7 was separated by HPLC eluting with heptane:isopropanol (60:40) on a Chiracel OD column to give the title enantiomers with an ee>80%.

Example 9

5-[(2,6-Difluoro-4-nitrophenyl)-1,2,4-triazol-1-ylmethyl]-3,3-dimethyl-3H-isobenzofuran-1-one A solution of Intermediate 1 (20.04 g) in anhydrous N,N-dimethylformamide (275 ml) was cooled to −14° under nitrogen and treated with potassium tert-butoxide in tetrahydrofuran (1M, 130 ml). After 1 h at 2.5°, 3,5-difluoronitrobenzene (9 ml) was added and stirring continued at 8° for 2 h.

In one modification of this general procedure, Intermediate 1 and 3,5-difluoronitrobenzene were dissolved in N,N-dimethylformamide, cooled to −11° and then treated with potassium tert-butoxide.

In another modification of this general procedure, a solution of Intermediate 1 and 3,5-difluoronitrobenzene in tetrahydrofuran was added to a cold (−30°) solution of potassium tert-butoxide in N,N-dimethylformamide.

The reaction mixture was poured into ethyl acetate (4 l), the organic phase separated and washed with brine (3×2 l) and concentrated to give a dark oil. The oil was purified by washing with ether and/or hexane.

Alternatively, the oil was purified by chromatography on silica gel 60 (E.M.Science) eluting with $CH_2Cl_2$: methanol (100:0→97:3). The appropriate fractions were combined and concentrated to give a yellow foam which was dissolved in $CH_2Cl_2$ (150 ml), washed with water (3×300 ml), concentrated and dried in vacuo to give the title compound as a yellow foam.

Alternatively the impure foam was recrystallised from methanol to give the title compound as a pale yellow crystalline solid.

HPLC and NMR data were consistent with the product obtained in Example 1 and with its structure.

The following examples illustrate pharmaceutical formulations according to the invention containing 5-[(2,6-difluoro-4-nitrophenyl)-1,2,4-triazol-1-ylmethyl]-3,3-dimethyl-3H-isobenzofuran-1-one as the active ingredient. Other compounds of the invention may be formulated in a similar manner.

Tablets for oral administration

| a) Direct Compression Tablet | |
|---|---|
| Component | Composition (%) |
| Active ingredient | 20.0 |
| Microcrystalline cellulose | 50.0 |
| Spray dried lactose | 24.2 |
| Sodium starch glycolate | 5.0 |
| Colloidal silicon dioxide | 0.3 |
| Magnesium stearate | 0.5 |

All materials except magnesium stearate are blended until sufficiently mixed. Magnesium stearate is screened and added to the mixture which is blended thoroughly. The resultant mix is compressed to predetermined tablet size and weight.

| b) Wet Granulation Tablet | |
|---|---|
| Component | Composition (%) |
| Active ingredient | 30.0 |
| Microcrystalline cellulose | 55.2 |
| Starch 1500 | 6.0 |
| Sodium starch glycolate | 5.0 |
| 10% polyvinylpyrrolidone in water | 3.0 |
| Magnesium stearate | 0.5 |
| Colloidal silicon dioxide | 0.3 |

All of the ingredients except for the polyvinylpyrrolidone solution and magnesium stearate are blended in a fluidized air bed. Polyvinylpyrrolidone solution is added to the blended powders with constant mixing until uniformly moist. After drying, the granules are milled to reduce particle size and increase size uniformity and blended with the magnesium stearate. The granules are then compressed to predetermined tablet size and weight.

Tablets of other strengths may be prepared by altering the ratio of active ingredient e.g. to lactose or altering the compression weight.

The tablets may be film-coated with suitable film-forming materials such as hydroxypropyl methylcellulose using standard techniques. Alternatively the tablets may be sugar coated or enteric coated.

| Syrup for oral administration | |
|---|---|
| Component | Composition (%) |
| Active ingredient, micronized | 5.00 |
| Magnesium aluminum silicate | 0.50 |
| Sodium carboxymethylcellulose | 0.80 |
| Sodium lauryl sulphate | 0.01 |
| Sorbitol solution, USP | 26.0 |
| Methylparaben | 0.20 |
| Propylparaben | 0.04 |
| Flavour | 0.50 |
| Purified water | 66.95 |

The sodium carboxymethylcellulose and magnesium aluminium silicate is hydrated in a solution of sodium lauryl sulphate in water for 24 hours. Active ingredient is suspended in the vehicle with the aid of a mixer. The preservatives are dissolved in the remaining water by heating and after cooling to room temperature, the sorbitol solution is added. The solution is added to the suspension, flavour mixed in and the pH adjusted as needed. The final suspension is mixed in a homogenizer.

| Soft gelatin capsules for oral administration | |
|---|---|
| Component | Composition (%) |
| Active ingredient, micronized | 5.0 |
| Polyethylene glycol | 47.5 |
| Propylene glycol | 47.5 |

The glycols are blended with warming until homogeneous. Active ingredient is added and the mixture homogenised and filled into an appropriate gelatin mass to give soft gelatin capsules containing the appropriate fill weight.

| Suppository for rectal administration | |
|---|---|
| Component | Composition (%) |
| Active ingredient, micronized | 2 |
| Witepsol W32, hard fat | 98 |

A slurry of the active ingredient in a portion of molten Witepsol (approximately 36° C.) is prepared using a high speed mixer and is then evenly dispersed in the remaining molten hard fat. The suspension is filled, using suitable machinery, into 1 or 2 g size suppository moulds and allowed to cool.

| Transdermal system | |
|---|---|
| Component | Composition (%) |
| Active ingredient | 5 |
| Silicone fluid | 90 |
| Colloidal silicon dioxide | 5 |

The silicone fluid and active ingredient are mixed together and the colloidal silicon dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene or polyvinyl acetate) or polyurethane, and an impermeable backing membrane made of a polyester multilaminate. The laminated sheet is then cut into patches.

Formulations for parenteral administration

| a) Intravenous solution | |
|---|---|
| Component | Composition (%) |
| Active ingredient | 5.0 |
| Sodium chloride USP | 0.9 |
| Phosphate buffer (monobasic and dibasic potassium phosphate) | 7.0 |
| Water for Injection USP | 87.1 |

Active ingredient is dissolved in the water with the remaining components and sterile filtered (0.22 μm filter). The solution is filled into glass vials, stoppered and sealed before autoclaving.

| b) Lyophilised product | |
|---|---|
| Component | Composition (%) |
| Active ingredient | 2.5 |
| Mannitol | 5.0 |
| Phosphate buffer (monobasic and dibasic potassium phosphate) | 7.0 |
| Water for Injection USP | 85.5 |

Active ingredient is dissolved in the water with the remaining components and sterile filtered (0.22 μm filter). The solution is filled into glass vials, stoppered and lyophilised before sealing. The lyophilised product is reconstituted with saline prior to administration.

We claim:

1. A compound of formula (I)

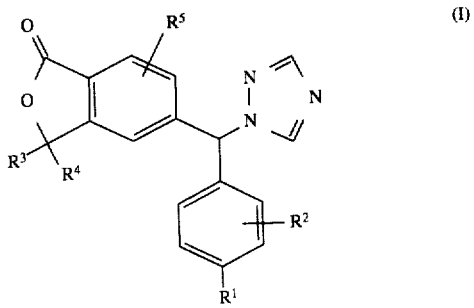

wherein $R^1$ represents a cyano or nitro group;

$R^2$ represents hydrogen or one or more halogen atoms;

$R^3$ represents a $C_{1-6}$alkyl group and $R^4$ represents hydrogen or a $C_{1-6}$alkyl group or $R^3$ and $R^4$ together represent a $C_{3-6}$cycloalkyl group; and $R^5$ represents hydrogen or one or more halogen atoms or $C_{1-6}$alkoxy groups or pharmaceutically acceptable salts or solvates thereof.

2. A compound as claimed in claim 1 wherein $R^2$ represents hydrogen or one or more halogen atoms selected from chlorine or fluorine.

3. A compound as claimed in claim 1 wherein $R^2$ represents hydrogen or one or two fluorine atoms in the meta position of the benzene ring relative to substituent $R^1$.

4. A compound as claimed in claim 1 wherein $R^3$ and $R^4$ each independently represent a $C_{1-6}$alkyl group.

5. A compound as claimed in claim 1 wherein $R^3$ and $R^4$ each represent a methyl group.

6. A compound as claimed in claim 1 wherein $R^5$ represents hydrogen or one or more halogen atoms selected from chlorine or fluorine or $C_{1-3}$alkoxy groups.

7. A compound as claimed in claim 1 wherein $R^5$ represents hydrogen or one or two fluorine atoms or methoxy groups.

8. A compound as claimed in claim 1 wherein $R^5$ is other than hydrogen and is in the 2 and/or 4-positions of the aromatic ring.

9. A compound as claimed in claim 1 wherein $R^5$ is hydrogen.

10. A compound as claimed in claim 1 wherein $R^1$ represents a cyano or nitro group, $R^2$ represents hydrogen or one or two fluorine atoms in the meta position of the benzene ring relative to substituent $R^1$, $R^3$ and $R^4$ each represent a methyl group and $R^5$ represents hydrogen.

11. 5-[(2,6-difluoro-4-nitrophenyl)-1,2,4-triazol-1-ylmethyl]-3,3-dimethyl-3H-isobenzofuran-1-one; 5-[(2-fluoro-4-nitrophenyl)-1,2,4-triazol-1-ylmethyl]-3,3-dimethyl-3H-isobenzofuran-1-one; 4-[(3,3-dimethyl-1-oxo-1,3-dihydro-isobenzofuran-5-yl)-1,2,4-triazol-1-ylmethyl]-3,5-difluorobenzonitrile; 5-[(4-nitrophenyl)-1,2,4-triazol-1-ylmethyl]-3,3-dimethyl-3H-isobenzofuran-1-one; 4-[(3,3-dimethyl-1-oxo-1,3-dihydro-isobenzofuran-5-yl)-1,2,4-triazol-1-ylmethyl]-3-fluorobenzonitrile; 4-[(3,3-dimethyl-1-oxo-1,3-dihydro-isobenzofuran-5-yl)-1,2,4-triazol-1-ylmethyl]-benzonitrile, or pharmaceutically acceptable salts or solvates thereof.

12. 5-[(2,6-difluoro-4-nitrophenyl)-1,2,4-triazol-1-ylmethyl]-3,3-dimethyl-3H-isobenzofuran-1-one, or pharmaceutically acceptable salts or solvates thereof.

13. A pharmaceutical composition comprising a compound of formula (I) as claimed in claim 1 or a pharmaceutically acceptable salt or solvate thereof as active ingredient together with one or more pharmaceutically acceptable carriers or excipients.

14. A pharmaceutical composition as claimed in claim 13 adapted for oral, rectal or topical administration.

15. A pharmaceutical composition comprising a compound as claimed in claim 10 which is formulated in unit dosage form comprising 0.1 to 200 mg of active ingredient.

16. A method for the treatment of a human or non-human mammal, comprising administration of an effective amount of a compound as claimed in claim 1 or a pharmaceutically acceptable salt or solvate thereof to lower oestrone and/or oestradiol levels.

17. A pharmaceutical composition comprising an effective amount of 5-[(2,6-difluoro-4-nitrophenyl)-1,2,4-triazol-1-ylmethyl]-3,3-dimethyl-3H-isobenzofuran-1-one or a pharmaceutically acceptable salt or solvate thereof, together with one or more pharmaceutically acceptable carriers or excipients.

18. A method for the treatment of a human or non-human mammal comprising administration of an effective amount of a composition according to claim 17.

* * * * *